United States Patent [19]

Pujado

[11] 4,284,583
[45] Aug. 18, 1981

[54] AMMOXIDATION PROCESS WITH EXTERNAL CATALYST REGENERATION ZONE

[75] Inventor: Peter R. Pujado, Palatine, Ill.

[73] Assignee: UOP Inc., Des Plaines, Ill.

[21] Appl. No.: 171,226

[22] Filed: Jul. 22, 1980

Related U.S. Application Data

[63] Continuation-in-part of Ser. No. 88,987, Oct. 29, 1979.

[51] Int. Cl.³ .................. C07C 120/14; B01J 37/12; F27B 15/08
[52] U.S. Cl. .................. 260/465 C; 252/416; 422/144
[58] Field of Search .............. 260/465 C; 252/416

[56] References Cited

U.S. PATENT DOCUMENTS

| | | | |
|---|---|---|---|
| 2,904,508 | 9/1959 | Hughes et al. | 208/311 |
| 3,186,955 | 6/1965 | Callahan et al. | 252/435 |
| 3,197,419 | 7/1965 | Callahan et al. | 252/456 |
| 3,200,084 | 8/1965 | Callahan et al. | 252/462 |
| 3,230,246 | 1/1966 | Callahan et al. | 260/465.3 |
| 3,446,833 | 5/1969 | Cavaterra et al. | 260/465.3 |
| 3,446,834 | 5/1969 | Cavaterra et al. | 260/465.3 |
| 3,472,892 | 10/1969 | Callahan et al. | 260/465.3 |
| 3,478,082 | 11/1969 | Huibers | 260/465.3 |
| 3,501,517 | 3/1970 | Hughes et al. | 260/465 |
| 3,639,103 | 2/1972 | Sheely | 23/288 S |
| 3,644,472 | 2/1972 | Paleologo et al. | 260/465.3 |
| 3,686,295 | 8/1972 | Grasselli et al. | 260/533 N |
| 3,691,224 | 9/1972 | Caporali et al. | 260/465.3 |
| 3,819,679 | 6/1974 | Sheely | 260/465.3 |
| 3,882,159 | 5/1975 | Callahan et al. | 260/465.3 |
| 3,991,096 | 11/1976 | Bortolini et al. | 260/465.3 |
| 4,052,333 | 10/1977 | Lee | 252/416 |

OTHER PUBLICATIONS

Heath, *Chemical Engineering*, pp. 80–81, Mar. 20, 1972.
Pujado et al., *The Oil and Gas Journal*, pp. 171–172, Jun. 6, 1977.
Ikeda et al., Chemical Engineering, pp. 53–55, Nov. 1, 1971.
Gelbein et al., American Institute of Chemical Engineering, (74th National Meeting) Mar. 1973.

*Primary Examiner*—Dolph H. Torrence
*Attorney, Agent, or Firm*—James R. Hoatson, Jr.; John F. Spears, Jr.; William H. Page, II

[57] ABSTRACT

A process for the ammoxidation of alkylaromatic hydrocarbons in a fluidized bed reactor is disclosed. A relatively small stream of catalyst is removed from an unsegregated single catalyst bed within the reaction zone and passed into a regeneration zone operated at a higher temperature. Metals on the catalyst are oxidized by contact in the regeneration zone with a preheated oxygen containing gas stream, which is then passed into the reaction zone. The residual oxygen in this gas stream may supply 15 percent or more of the oxygen consumed in the reaction zone. The continuous regeneration maintains the metals on the catalyst in a high oxidation state.

13 Claims, 1 Drawing Figure

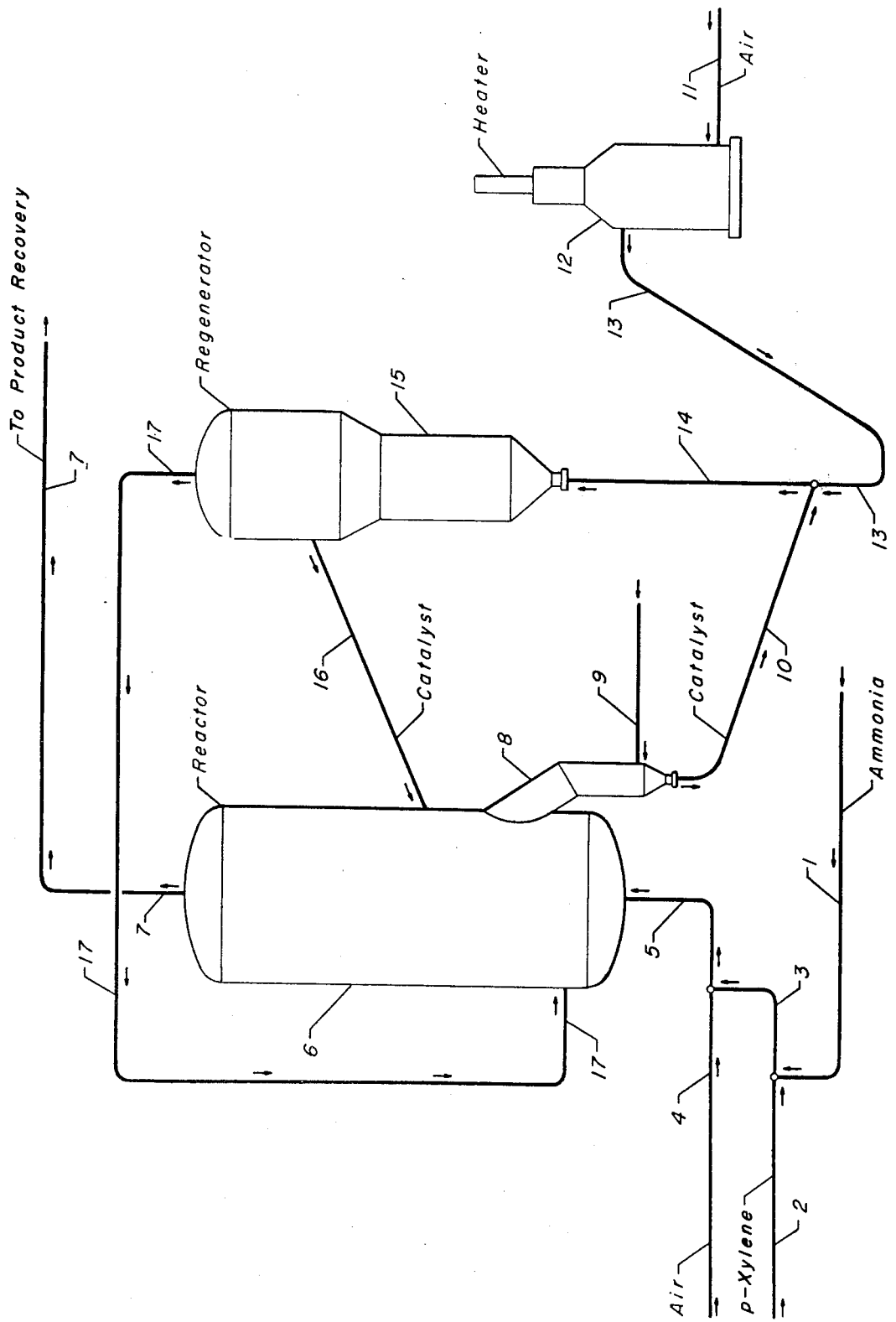

AMMOXIDATION PROCESS WITH EXTERNAL CATALYST REGENERATION ZONE

CROSS REFERENCE TO RELATED APPLICATION

This application is a continuation-in-part of my prior copending application, Ser. No. 88,987, filed Oct. 29, 1979. The entire teaching of my prior application is incorporated herein.

FIELD OF INVENTION

The invention relates to a hydrocarbon conversion process. The invention more specifically relates to an improved process for the ammoxidation of alkylaromatic hydrocarbons to the corresponding nitriles in a reaction zone containing a fluidized catalyst bed. The invention is specifically directed to the regeneration of the catalyst used within the reaction zone. References describing ammoxidation processes are concentrated in Class 260, especially Class 260-465, and in Class 23-288.

PRIOR ART

The overall flow of a representative process for the production of acrylonitrile by the ammoxidation of propylene is described in an article at page 80 of Mar. 20, 1972 edition of *Chemical Engineering* and in an article at page 171 of the June 6, 1977 edition of *The Oil and Gas Journal*. A generalized description of a process for the production of isophthalonitrile by the ammoxidation of m-xylene is presented in an article at page 53 of the Nov. 1, 1971 edition of *Chemical Engineering*. These references illustrate the flow scheme of an ammoxidation process including the various product recovery and purification steps. A process in which terephthalonitrile is produced as an intermediate product is described in a paper by A. P. Gelbein el al presented at the March 1973 national meeting of the American Institute of Chemical Engineering.

Catalysts which may be used in the ammoxidation process are described in U.S. Pat. No. 2,904,508 (Cl. 260-465.3); U.S. Pat. No. 3,230,246 (Cl. 260-465.3); U.S. Pat. No. 3,186,955 (Cl. 252-435); U.S. Pat. No. 3,197,419 (Cl. 252-456); 3,186,955 (Cl. 252-435); U.S. Pat. No. 3,197,419 (Cl. 252-456); U.S. Pat. No. 3,198,750 (Cl. 252-456); U.S. Pat. No. 3,200,081 (Cl. 252-443); U.S. Pat. No. 3,200,084 (Cl. 252-462); U.S. Pat. No. 3,446,833 (Cl. 260-465.3); U.S. Pat. No. 3,446,834 (Cl. 260-465.3); U.S. Pat. No. 3,686,295 (Cl. 260-533N); and U.S. Pat. No. 3,892,794 (Cl. 260-465.3). These patents also provide general descriptions of the reactants, operating conditions and operating procedures of the ammoxidation process.

The regeneration of ammoxidation catalysts is the general subject of U.S. Pat. Nos. 3,882,159 (Cl. 260-465.3) and U.S. Pat. No. 4,052,333 (Cl. 252-416). The former reference teaches the benefits of adding an inert support material containing molybdenum during the regeneration of molybdenum-containing oxidation catalysts. The latter reference attributes beneficial regeneration results to the heating of the catalyst in an atmosphere which comprises 20–45% by volume of steam, with the balance being air or inert gas.

U.S. Pat. No. 3,691,224 (Cl. 260-465.3) describes the regeneration of ammoxidation catalysts within the dip leg or exhaust tube through which catalyst descends from the cyclone used at the top of the reactor. U.S. Pat. No. 3,230,246 (Cl. 260-465.3) describes an ammoxidation reactor and various elements which may be used within the reactor. U.S. Pat. No. 3,644,472 (Cl. 260-465.3) presents an ammoxidation process utilizing finned heat removal tubes to divide the fluidized catalyst bed into smaller beds, each of which has a height to diameter ratio between 5:1 and 20:1. It is believed that these references do not teach or suggest the use of an isolated regeneration zone which receives a high temperature oxygen-containing stream. It is also believed that they do not suggest the overall flow scheme of the subject process or the regeneration technique of the subject process.

U.S. Pat. No. 3,472,892 (Cl. 260-465.3); U.S. Pat. No. 3,501,517 (Cl. 260-465); U.S. Pat. No. 3,639,103 (Cl. 23-288S); U.S. Pat. No. 3,819,679 (Cl. 260-465.3) present diagrams of reaction zones for the ammoxidation process. These references teach the use of a disengagement zone above the dense bed of fluidized catalyst or the use of a quench zone above the reaction zone. The external vessel of U.S. Pat. No. 3,472,892 is a separatory vessel which receives catalyst from the regeneration zone. This reference indicates the catalyst delivered from the separatory vessel is "cool" and may be used to hold down the temperature of the quench zone.

U.S. Pat. No. 3,478,082 (Cl. 260-465.3) presents a process for the production of nitriles by the reaction of olefins and ammonia which utilizes a catalyst regeneration zone which is isolated from the reactor. This isolation is the result of the reaction being performed in the absence of free oxygen. The catalyst is reoxidized in the regeneration zone and used to transport oxygen into the reaction zone. The reference distinguishes itself from the ammoxidation process of the subject invention.

BRIEF SUMMARY OF THE INVENTION

The invention provides an improved ammoxidation process which maintains the catalyst at a high level of activity for extended periods. The inventive concept includes the continuous reoxidation of the metals on a small stream of catalyst withdrawn from the reaction zone and returned to the reaction zone after reoxidation. The metals reoxidation is effected by contacting the catalyst with air which has been preheated in a furnace.

One broad embodiment of the invention may be characterized as a process for the ammoxidation of unsaturated cyclic hydrocarbons which comprises the steps of passing a feed stream which comprises an alkylaromatic $C_7$-$C_{10}$ hydrocarbon into the lower one-half of a reaction zone which is maintained at ammoxidation conditions including a temperature between 350° C. and 550° C. and which contains a fluidized bed of catalyst; passing a first oxygen-containing stream and ammonia into the lower one-half of the reaction zone; removing from the reaction zone an effluent comprising an aromatic nitrile and recovering the aromatic nitrile; transferring a stream of used catalyst from the reaction zone to an isolated regeneration zone which is maintained at catalyst oxidation conditions including a temperature between 350° C. and 550° C. and which contains a fluidized bed of catalyst; heating a second oxygen-containing stream to a temperature above 350° C. and passing the second air stream into the regeneration zone; removing from the regeneration zone a regeneration zone effluent stream which comprises 10 mole percent oxygen and passing the regeneration zone effluent stream into the reaction zone as a third oxygen-containing stream which supplies at least 8 mole percent of the total oxygen consumed within the reaction zone; and transferring a stream of regenerated catalyst from the regeneration zone to the reaction zone.

DESCRIPTION OF THE DRAWING

The Drawing illustrates the use of the inventive concept in the ammoxidation of paraxylene to produce terephthalonitrile. A stream of ammonia from line 1 is admixed with a feed stream of paraxylene from line 2 and passed into line 3. The contents of line 3 are admixed with a stream of air from line 4 to form a vapor phase feed stream which is passed into the reactor 6 through line 5. The feed stream passes upward through a porous grid or other vapor distributor located near the bottom of the reactor and rises through a single fluidized bed of catalyst located within the reactor. A vapor stream containing the reaction products, by-products, any residual reactants, and nitrogen from the air which was charged to the reactor is removed from the reactor in line 7 and passed to facilities for the recovery of the terephthalonitrile.

A small portion of the total catalyst inventory of the reactor is slowly withdrawn into a vertical side leg 8 which contains a number of slanted baffles. A small stream of nitrogen or steam or similar inert gas from line 9 is passed into the lower portion of the side leg to strip hydrocarbons from the entering catalyst. The catalyst is then allowed to pass downward through line 10 at a rate which may be controlled by a slide valve located in line 10. A second air stream from line 11 is heated in the heater 12 to a temperature above 350° C. This heated air stream is passed through line 13 to the junction with line 10 and is used to transport the catalyst from line 10 upward through a riser 14 into a regenerator 15. The regenerator is operated at a higher average temperature than the reactor.

A portion of the oxygen which is contained in the preheated air stream is consumed in the oxidation of the metals on the catalyst. However, there is essentially no carbon combustion within the regenerator since the catalyst is essentially free of coke. The residue of the preheated air stream is separated from the fluidized catalyst bed maintained within the regenerator in a cyclone or other separation means not shown and passed through line 17 into the reactor 6. The oxygen contained within this vapor stream is a significant portion of the total oxygen consumed within the reactor. A stream of highly oxidized catalyst is passed through line 16 at a rate controlled by a means not shown from the regenerator to the reactor. The rate of flow of this highly oxidized catalyst is controlled in a manner which maintains the desired overall oxidation level of the metals on the catalyst within the reactor.

The Drawing illustrates one embodiment of the invention which is used for the ammoxidation of a specific hydrocarbon. This depiction of one embodiment of the invention is not intended to exclude from the inventive concept other embodiments set out herein or which are the result of normal and reasonable modification of those embodiments. For simplicity and clarity, a number of pieces of apparatus normally required in the operation of the process have not been shown. This deleted apparatus includes pressure, flow and temperature control systems, vessel internals, etc., all of which may be of customary design.

DETAILED DESCRIPTION

Ammoxidation processes are used commercially to produce unsaturated nitriles from acyclic olefinic hydrocarbons and aromatic nitriles from alkyl-substituted aromatic hydrocarbons. The most widely practiced of these processes is the ammoxidation of propylene in a fluidized bed reactor to produce acrylonitrile. Other ammoxidation processes are the production of terephthalonitrile from paraxylene and isophthalonitrile from metaxylene. The catalyst used in these processes suffers from gradual deactivation, which is attributed to the reduction of the oxidized metals contained in the catalyst to less highly oxidized states. It is believed that highly oxidized metals are necessary in highly active catalyst because oxygen from the catalyst is consumed in the ammoxidation reaction, with the catalytic metals then being reoxidized by the oxygen which is charged to the reaction zone.

Because of the sizable oxygen concentrations in the reaction zone, coke deposition on the catalyst is not a problem as it is in some fluidized bed processes such as the fluidized catalytic cracking of petroleum fractions. The catalyst therefore remains relatively clean while it is being used. The gradual deactivation of the ammoxidation catalyst does, however, still occur and is an important operating and economic factor in ammoxidation processes. This deactivation appears to possibly operate by several mechanisms which are related to the reduction of the catalyst within the reaction zone.

It is an objective of the subject invention to provide an improved fluidized bed ammoxidation process. It is a further objective of the subject invention to provide a process for the production of terephthalonitrile by the reaction of p-xylene, ammonia and oxygen in a reaction zone containing a fluidized bed of catalyst. It is a specific objective of the invention to provide an improved continuous catalyst regeneration method for an ammoxidation process.

It has been found that the activity of the ammoxidation catalyst may be maintained at a high level by continuously reoxidizing a small stream of catalyst withdrawn from the reaction zone. If the reoxidation of the catalyst is performed within a relatively short time after the catalyst has been put on stream and is done at the proper conditions, then the catalyst is returned to essentially its original level of activity. The proper reoxidation of the catalyst becomes increasingly more difficult the longer the catalyst has been on stream. Exhausted catalyst (highly or totally reduced) cannot be restored to its original state and exhibits only a brief reactivation when reoxidized at the preferred conditions. The subject invention provides a means to continuously regenerate a controlled amount of the catalyst by reoxidation of the metals and thereby provides an improved ammoxidation catalyst. In the subject process, both the frequency of regeneration and the regeneration conditions can be closely controlled to optimize the regeneration.

The feed hydrocarbon passed into the reaction zone may be any readily vaporizable $C_7$–$C_{10}$ alkyl-substituted aromatic hydrocarbon. Preferred feed hydrocarbons are paraxylene for the production of terephthalonitrile and metaxylene for the production of isophthalonitrile. Other hydrocarbons which may be charged to the subject process include toluene, orthoxylene, mesitylene, α-methyl-naphthalene and homologs of these hydrocarbons. For instance, benzonitrile is produced from toluene, and orthophthalonitrile is produced from orthoxylene. The subject process may also be used for the ammoxidation of acyclic $C_3$–$C_8$ hydrocarbons, such as propylene, as described in my prior application.

The feed hydrocarbon is passed into a reaction zone and admixed with the oxygen and ammonia. This admixture of the three reactants can be achieved in several different sequences. Preferably, the hydrocarbon and ammonia are admixed with at least some of the oxygen prior to passage of the reactants into the reaction zone. Another method is to admix the hydrocarbon and ammonia and then pass this bi-component mixture into the reaction zone, with the oxygen entering the reaction zone separately. The reactants may be distributed within the reaction zone at more than one location. Care must be taken to avoid the formation of an explosive mixture at any location at which there is not sufficient catalyst present to suppress an explosion. It is therefore highly preferred that a portion of the air be passed into the reaction zone at a point within the catalyst bed to avoid forming an explosive mixture in the feed line. Following the inventive concept, at least a portion of the oxygen which enters the reaction zone is contained in the high temperature effluent stream of the regeneration zone. It is also highly preferred, but not required, that a third oxygen-containing stream is passed into the reaction zone to reduce the oxygen content of the hydrocarbon-containing feed stream. This third stream would be formed by diverting a portion of the air shown entering the reactor via line 4 of the Drawing into line 17.

The reaction zone is preferably in the shape of a vertically oriented closed cylinder which is not enlarged at the top. The majority of the reactants is preferably passed upward into the catalyst bed through a porous grid which extends across the interior of the reactor near the bottom of the reactor. The preferred grid has coverings directly over the vapor passageways, as in bubble caps used in fractionation columns, to aid in retaining the catalyst above the grid. A single bed of fluidized catalyst is preferred. That is, the catalyst bed is preferably not segregated into vertically stacked zones or layers by horizontal perforated grids or other means, although such an arrangement is possible and may be utilized in those instances when a well defined distribution of residence times is desired. Since the ammoxidation reaction is highly exothermic, indirect heat exchange means are preferably provided at several points within the reaction zone at points which are within the fluidized mass of catalyst. The preferred heat removal medium is water, which is converted to steam used within various product recovery steps. Further details on the removal of heat from the reaction zone may be obtained by reference to U.S. Pat. No. 3,991,096.

For reasons of economy, the preferred source of the oxygen consumed within the reaction zone is air. However, other oxygen-containing gas streams including relatively pure oxygen streams may also be charged to the reaction zone.

While the process is being performed, the reaction zone is maintained at ammoxidation conditions. The pressure within the reaction zone is normally maintained within the range of from atmospheric to about 6.0 atmospheres gauge, with a pressure less than 2.0 atmospheres gauge being preferred. The average temperature required within the reaction zone will be dependent on such variables as the catalyst, the present catalyst activity, the desired conversion rates and the particular hydrocarbon being charged to the process. A general range of temperatures is from about 350° C. to 550° C. A preferred range of temperatures is from 420° C. to 480° C. The residence time of the hydrocarbonaceous reactant within the reaction zone should be within the range of from about 0.5 to about 10.0 seconds, with a residence time between 3 and 6 seconds being preferred. The linear gas velocity within the reaction zone should be between about 25 and 60 cm/sec based on the cross-sectional area of an empty reaction zone. It is preferred that only a minimal disengagement zone is provided within the upper portion of the reaction zone and that no quench zone is employed within the vessel housing the reaction zone.

The amounts of both oxygen and ammonia charged to the reaction zone are preferably in slight excess of those consumed within the reaction zone. The ammoxidation of the feed hydrocarbon is not totally selective and some of the hydrocarbon may be consumed in side reactions. The ammonia is not consumed in these reactions or by the products of these reactions. It may therefore not be necessary to supply more than the stoichiometric amount of ammonia to the reaction zone. The amount of ammonia and oxygen which is required will be dependent on the number of points at which the feed hydrocarbon is being ammoxidated. A xylene would therefore require more of each of these reactants than toluene if both of the available methyl group were being ammoxidated. The molar ratio of hydrocarbon to ammonia is preferably between 1:0.9 and 1:3.0. The molar ratio of hydrocarbon to oxygen is preferably within the range of from 1:1.5 to about 1:4.5. The preferred ratio will vary depending on the nature of the hydrocarbon feed stock. The use of a lower ammonia feed rate by the recycling of HCN to the reaction zone is taught in U.S. Pat. No. 3,819,679.

The catalyst should be readily fluidizable at the ammoxidation conditions maintained within the reaction zone. Catalysts having particle sizes up to 1,000 microns may be used, but the average particle size is preferably between 20 and 150 microns. The catalyst is retained within a single fluidized bed which occupies the great majority of the reaction zone. The catalyst bed is preferably not divided into zones or sub-beds by foraminous members, grates or screens.

The regeneration zone is preferably a vertically oriented closed cylinder which is located outside of the vessel which contains the reaction zone. An arrangement of the vessels similar to that shown in the Drawing is preferred. The two zones are connected by two catalyst transfer lines. One of the catalyst transfer lines carries used catalyst from the reaction zone to the regeneration zone and also serves as a riser-type contacting zone in which the initial contacting of the used catalyst and preheated air occurs. The rate of catalyst circulation is preferably controlled by a single slide value which controls the rate of catalyst removal from the reaction zone. The rate of catalyst circulation should be sufficient to provide an average catalyst residence time within the reaction zone between regenerations of less than two weeks but longer than one day, with an average residence time of between three and seven days being preferred. A second valve may be employed if desired to control the rate of catalyst flow from the regeneration zone to the reaction zone. However, it is preferred that the catalyst be allowed to spill over from the regeneration zone into the reaction zone at a rate set by a level control system within the main vessel of the regeneration zone. The catalyst withdrawn from the reaction zone is preferably stripped of hydrocarbons by nitrogen or steam to minimize the passage of hydrocarbons into the regeneration zone. The flow of gas from the regeneration zone to the reaction zone through the catalyst transfer line should be minimized through proper design of the transfer line and catalyst collection system. The regeneration zone is operated at a pressure just slightly above that in the reaction zone to force the vaporous effluent stream of the regeneration zone to always flow into the reaction zone. The temperature maintained in the regeneration zone is preferably above that maintained in the reaction zone. Unless otherwise specified, all temperatures refer to average catalyst bed temperatures. A general range of temperatures for use in the regeneration zone is from 460° C. to 575° C. However, it is very much preferred to operate the regeneration zone at a temperature between 500° C. and 540° C.

Only a small amount of heat of combustion is liberated within the regeneration zone because of the very low carbon content of the used catalyst. The air, or other oxygen-containing stream, which is passed into the regeneration zone is therefore preheated to the temperature required to maintain the regeneration zone at the desired temperature. This stream is passed through a heater such as a direct fired air heater or an indirect fired furnace prior to contact with the used catalyst. The regeneration zone air stream is thereby heated to a temperature above 350° C. and preferably above 400° C. and below 600° C. before being passed into the regeneration zone. The upward vapor velocity through the regeneration zone should be sufficient to fluidize the catalyst bed, but only minimal fluidization is required. The regeneration zone vessel should be of sufficient size to allow the catalyst to have an average residence time within the regeneration zone of from one to about four hours. An average residence time of about two hours is preferred.

A large portion of the oxygen which enters the regeneration zone is not consumed and therefore leaves the regeneration zone as a component of the regeneration zone effluent stream. The regeneration zone effluent stream will therefore normally contain 10 mole percent oxygen and may contain 15 or more mole percent oxygen. The flow rate of this stream is preferably sufficient that it will supply at least 8 and possibly more than 15 mole percent of the total oxygen consumed in the reaction zone. The small amount of carbon combustion in the regeneration zone will result in the carbon oxide content of the regeneration zone effluent stream being relatively low. The total carbon oxide (carbon monoxide and carbon dioxide) content of the regeneration zone effluent stream should be below 10 mole percent and is preferably below 5 mole percent. Some combustion of hydrocarbons will occur in the regeneration zone. These hydrocarbons are present in any gas which passes into the regeneration zone from the reaction zone and may include hydrocarbons adhering to the surface of catalyst entering the regeneration zone. Less than 1.0 mole percent of the oxygen passed into the regeneration zone is consumed in the oxidation of carbon carried into the regeneration zone as carbon deposits on the used catalyst when the process is being performed properly.

The reaction zone effluent stream and the regeneration zone effluent stream should both pass through particle separation zones as they leave their respective zones. These separation zones may be located within the respective zones or outside of these zones. The particle separation zones are preferably one or more multiple stage cyclones. A two- or three-stage cyclone is preferred. Any other type of solid-vapor separation device of suitable efficiency and reliability may be employed if desired. The particles which enter the separation zone should be returned to the catalyst bed through a conduit which delivers the catalyst within a dense-phase portion of the catalyst bed.

The catalyst which may be employed have been well described in the available prior art including those references cited above. Ammoxidation catalysts are normally composed of several metals in the form of their oxides. The catalyst may or may not include a support material. A preferred support material is silica and if employed would comprise about 75 wt.% of the catalyst. The preferred catalyst contains at least one metallic component chosen from the group consisting of molybdenum, phosphorus, bismuth, antimony, iron, nickel and copper. More preferably, the catalyst also contains at least one metallic component chosen from the group consisting of tungsten, vanadium, cerium, bismuth, tin, tellurium, rhenium and cobalt.

I claim as my invention:

1. A process for the ammoxidation of alkylaromatic hydrocarbons which comprises the steps of:
    (a) passing a feed stream which comprises an alkylaromatic hydrocarbon into the lower one-half of a reaction zone which is maintained at ammoxidation conditions including a temperature of between 350° C. and 550° C. and which contains a fluidized bed of catalyst;
    (b) passing a first oxygen-containing stream and ammonia into the lower one-half of the reaction zone;
    (c) removing from the reaction zone an effluent comprising an aromatic nitrile and recovering the aromatic nitrile;
    (d) transferring a stream of used catalyst from the reaction zone into an isolated regeneration zone which is maintained at catalyst oxidation conditions including a temperature between 350° C. and 550° C. and which contains a fluidized bed of catalyst;
    (e) heating a second oxygen-containing stream to a temperature above 350° C. and passing the second air stream into the regeneration zone;
    (f) removing from the regeneration zone a regeneration zone effluent stream which comprises at least 10 mole percent oxygen and passing the regeneration zone effluent stream into the reaction zone as a third oxygen-containing vapor stream which supplies at least 8 mole percent of the total oxygen consumed within the reaction zone; and,
    (g) transferring a stream of regenerated catalyst from the regeneration zone to the reaction zone.

2. The process of claim 1 further characterized in that less than 1 mole percent of the oxygen contained in the second oxygen-containing stream is consumed within the regeneration zone in the oxidation of carbon carried into the regeneration zone as carbon deposits on the used catalyst.

3. The process of claim 1 further characterized in that the average temperature maintained in the regeneration zone is higher than the average temperature maintained in the reaction zone.

4. The process of claim 3 further characterized in that the third oxygen-containing stream supplies at least 15 mole percent of the total oxygen consumed in the reaction zone.

5. The process of claim 4 further characterized in that the regeneration zone effluent stream contains less than 5 mole percent carbon oxides.

6. The process of claim 4 further characterized in that the oxygen-containing stream is heated to a temperature above 400° C. prior to being passed into the regeneration zone.

7. The process of claim 6 further characterized in that the reaction zone contains a single fluidized bed of catalyst.

8. The process of claim 6 further characterized in that the feed stream comprises paraxylene.

9. The process of claim 6 further characterized in that the feed stream comprises metaxylene.

10. The process of claim 6 further characterized in that the catalyst comprises at least one component chosen from the group consisting of molybdenum, phosphorus, antimony, iron, nickel and copper.

11. The process of claim 10 further characterized in that the catalyst comprises at least one element chosen from the group consisting of tungsten, vanadium, cerium, bismuth, tin, tellurium, rhenium and cobalt.

12. The process of claim 10 further characterized in that the regeneration zone is maintained at a temperature above 500° C. and in that the reaction zone is operated at a temperature below 480° C.

13. The process of claim 12 further characterized in that the reaction zone contains a single fluidized bed of catalyst.

* * * * *